United States Patent
Yanagi et al.

(10) Patent No.: US 7,473,666 B2
(45) Date of Patent: Jan. 6, 2009

(54) PARTICULATE POROUS AMMOXIDATION CATALYST

(75) Inventors: Hiroyuki Yanagi, Kurashiki (JP); Hideo Midorikawa, Kurashiki (JP); Tutomu Ueda, Kurashiki (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 375 days.

(21) Appl. No.: 10/541,393

(22) PCT Filed: Feb. 27, 2004

(86) PCT No.: PCT/JP2004/002397

§ 371 (c)(1),
(2), (4) Date: Jul. 1, 2005

(87) PCT Pub. No.: WO2004/078344

PCT Pub. Date: Sep. 16, 2004

(65) Prior Publication Data

US 2006/0155139 A1   Jul. 13, 2006

(30) Foreign Application Priority Data

Mar. 5, 2003   (JP) .............................. 2003-057968

(51) Int. Cl.
  *B01J 21/00* (2006.01)
  *B01J 23/00* (2006.01)
  *B01J 23/10* (2006.01)
  *B01J 23/58* (2006.01)
  *B01J 23/70* (2006.01)
  *C07C 253/00* (2006.01)

(52) U.S. Cl. ............ 502/243; 502/249; 502/255; 502/258; 502/233; 502/302; 502/304; 502/311; 502/316; 502/317; 502/321; 502/330; 502/338; 502/353; 502/355; 558/320; 558/321; 558/325

(58) Field of Classification Search ......... 502/204, 502/210, 215, 214, 232–263, 300–355; 558/320, 558/321, 325
See application file for complete search history.

(56) References Cited

U.S. PATENT DOCUMENTS

| 3,397,153 A | | 8/1968 | Sippel | |
|---|---|---|---|---|
| 4,264,476 A | * | 4/1981 | Umemura et al. | 502/242 |
| 4,370,279 A | | 1/1983 | Sasaki et al. | |
| 4,892,856 A | * | 1/1990 | Kawajiri et al. | 502/247 |
| 5,658,842 A | * | 8/1997 | Midorikawa et al. | 502/314 |
| 5,663,113 A | * | 9/1997 | Midorikawa et al. | 502/314 |
| 6,479,691 B1 | * | 11/2002 | Sasaki et al. | 558/321 |
| 6,596,897 B1 | * | 7/2003 | Guan et al. | 558/323 |
| 7,288,669 B2 | * | 10/2007 | Gaffney et al. | 558/320 |
| 2002/0103077 A1 | * | 8/2002 | Kimura et al. | 502/305 |
| 2002/0188149 A1 | * | 12/2002 | Bogan et al. | 558/321 |
| 2003/0208085 A1 | * | 11/2003 | Gaffney et al. | 558/321 |

FOREIGN PATENT DOCUMENTS

| EP | 0 153 077 | 8/1985 |
|---|---|---|
| GB | 1 553 801 | 10/1979 |
| GB | 2 030 885 | 4/1980 |
| JP | 38-19111 | 9/1960 |
| JP | 38-17967 | 12/1960 |
| JP | 57-075147 | 5/1982 |
| JP | 57-56373 | 11/1982 |
| JP | 58-113141 | 5/1983 |
| JP | 60-166037 | 8/1985 |
| JP | 2-47264 | 10/1990 |
| JP | 2002-219362 | 8/2002 |
| JP | 57-119837 | 7/2005 |
| WO | WO 03/039744 | 5/2003 |

OTHER PUBLICATIONS

Hinako et al. JP2002-219362: abstract, machine translation and drawings. Patent Abstracts of Japan. Jun. 8, 2002.*
Hiroshi Otouma et al., "The Effect of Micropore Structure of Catalyst Upon the Ammoxidation of Isobutene", Reports Res. Lab. Asahi Glass Co., 34 (1984), pp. 183-196.

* cited by examiner

Primary Examiner—Steven Bos
Assistant Examiner—Anthony J Zimmer
(74) Attorney, Agent, or Firm—Staas & Halsey LLP

(57) ABSTRACT

A particulate porous ammoxidation catalyst for use in producing acrylonitrile or methacrylonitrile by reacting propylene, isobutene or tert-butyl alcohol with molecular oxygen and ammonia in a fluidized-bed reactor, the catalyst comprising a metal oxide and a silica carrier having supported thereon the metal oxide, wherein the metal oxide contains at least two elements selected from the group consisting of molybdenum, bismuth, iron, vanadium, antimony, tellurium and niobium, and the catalyst having a particle diameter distribution wherein the amount of catalyst particles having a particle diameter of from 5 to 200 μm is from 90 to 100% by weight, based on the weight of the catalyst, and having a pore distribution wherein the cumulative pore volume of pores having a pore diameter of 80 Å or less is not more than 20%, based on the total pore volume of the catalyst and wherein the cumulative pore volume of pores having a pore diameter of 1,000 Å or more is not more than 20%, based on the total pore volume of the catalyst. A method for efficiently producing this catalyst.

6 Claims, No Drawings

PARTICULATE POROUS AMMOXIDATION CATALYST

CROSS REFERENCE TO RELATED APPLICATIONS

This application is based on and hereby claims priority to PCT application No. PCTJP2004/102397 filed Feb. 27, 2004 and Japanese Application No. 2003-057968 filed Mar. 5, 2003, the contents of which are hereby incorporated by reference.

BACKGROUND OF THE INVENTION

1. Field of the Invention

The present invention relates to a particulate porous ammoxidation catalyst which can be advantageously used in producing acrylonitrile or methacrylonitrile by reacting propylene, isobutene or tert-butyl alcohol with molecular oxygen and ammonia in a fluidized-bed reactor. More particularly, the present invention is concerned with a particulate porous ammoxidation catalyst which comprises a metal oxide and a silica carrier having supported thereon the metal oxide, wherein the metal oxide contains at least two elements selected from the group consisting of molybdenum, bismuth, iron, vanadium, antimony, tellurium and niobium, the catalyst having a particle diameter distribution wherein the amount of catalyst particles having a particle diameter of from 5 to 200 μm is from 90 to 100% by weight, based on the weight of the catalyst, and having a pore distribution wherein the cumulative pore volume of pores having a pore diameter of 80 Å or less is not more than 20%, based on the total pore volume of the catalyst, and the cumulative pore volume of pores having a pore diameter of 1,000 Å or more is not more than 20%, based on the total pore volume of the catalyst. The present invention is also concerned with a method for efficiently producing this catalyst. The ammoxidation catalyst of the present invention exhibits not only high activity in producing the desired product but also high attrition resistance when used on a commercial scale. Therefore, the catalyst of the present invention is advantageous in that, when the catalyst of the present invention is used for performing a catalytic ammoxidation of propylene, isobutene or tert-butyl alcohol in a fluidized-bed reactor, acrylonitrile or methacrylonitrile can be produced stably in high yield.

2. Prior Art

It has been well known to produce acrylonitrile or methacrylonitrile by ammoxidation of propylene, isobutene or tert-butyl alcohol, namely, a reaction of propylene, isobutene or tert-butyl alcohol with molecular oxygen and ammonia. A number of proposals have been made with respect to catalysts for use in the ammoxidation of propylene, isobutene or tert-butyl alcohol. For example, Examined Japanese Patent Application Publication No. Sho 38-17967 proposes an oxide catalyst containing molybdenum, bismuth and iron, and Examined Japanese Patent Application Publication No. Sho 38-9111 proposes an oxide catalyst containing antimony and iron. Further, various improvements have been proposed with respect to these ammoxidation catalysts.

A number of proposals have been made to improve an ammoxidation catalyst by changing the composition thereof, and such proposals have contributed to the improvement of the catalyst performance. However, there have not been made many proposals to improve an ammoxidation catalyst by changing the physical structure of the catalyst. As examples of prior art documents disclosing such proposals, there can be mentioned Examined Japanese Patent Application Publication No. Sho 57-56373 (corresponding to U.S. Pat. No. 4,264,476) which discloses a catalyst for ammoxidation of propylene, containing molybdenum, bismuth, iron, cobalt and zirconium as essential components, and Unexamined Japanese Patent Application Laid-Open Specification No. Sho 57-75147 which discloses a catalyst for ammoxidation of propylene, containing molybdenum, bismuth and antimony as essential components, wherein, in each of these catalysts, the amount of silica carrier, average pore diameter, total pore volume and specific surface area are, respectively, in specific ranges.

Each of the above-mentioned two patent documents (in which it is attempted to improve the catalyst performance by changing the physical structure of the catalyst) discloses a catalyst (having a specific physical structure) for use in producing acrylonitrile in a fluidized-bed reactor. However, there are no disclosures about the pore distributions of the catalysts in these two patent documents.

On the other hand, proposals paying attention to the pore distribution of an oxide catalyst, have been made in the following patent documents. Unexamined Japanese Patent Application Laid-Open Specification No. Sho 57-119837 discloses a catalyst for use in the oxidation of an olefin in a fixed-bed reactor, wherein the catalyst has an average pore radius of 2,000 Å or more. Unexamined Japanese Patent Application Laid-Open Specification No. Sho 58-113141 (corresponding to GB 2030885A) discloses a process for producing methacrolein. Claim 3 of this patent document describes that the cumulative surface area of pores having a diameter smaller than 100 Å is not more than 3%, based on the surface area of the catalyst. International patent application publication No. WO03/039744 discloses a metal oxide catalyst for use in the commercial production of acrolein or acrylic acid by oxidation of propylene, wherein the physical structure (including the pore distribution) of the catalyst is specified in detail.

However, none of these oxide catalysts can be used in a fluidized-bed reactor. Specifically, in the above-mentioned Unexamined Japanese Patent Application Laid-Open Specification No. Sho 57-119837, claim 1 describes that the catalyst is for use in a fixed-bed reactor. Further, the catalyst of this patent document has an average pore radius as large as 2,000 Å or more and, hence, it is presumed that the catalyst exhibits poor mechanical strength. Also, the catalyst of this patent document is an extrusion-molded product (e.g., a cylinder-shaped article having a diameter of 4 mm and a length of from 4 to 8 mm in the working examples) and, hence, it is presumed that the catalyst exhibits poor fluidity. Therefore, it is apparent that the catalyst disclosed in this patent document cannot be used in a fluidized-bed reactor. The above-mentioned Unexamined Japanese Patent Application Laid-Open Specification No. Sho 58-113141 discloses a process for producing methac-rolein, wherein the mode of reaction is not specified. However, in the working examples of this patent document, there is a description that the catalyst is obtained as a pellet having a diameter of 4.8 mm and, hence, it is apparent that the catalyst proposed in this patent document exhibits poor fluidity and is for use in a fixed-bed reactor. Therefore, this catalyst cannot be used in a fluidized-bed reactor. In the above-mentioned international patent application publication No. WO03/039744, the mode of reaction is not specified; however, the catalyst proposed in this patent document has a pore distribution wherein the cumulative pore volume of pores having a pore diameter of from 0.1 to 1 μm is as large as not less than 20%, based on the total pore volume of the catalyst. That is, the ratio of pores having a large diameter is great in the pore distribution of this catalyst and, hence, it is presumed that this catalyst exhibits poor mechanical strength. Further, in the working examples of this patent document, there is a description that a particulate catalyst precursor is pelletized in the form of a tablet having a diameter of 5 mm and a height of 4 mm. Therefore, it is presumed that the catalyst exhibits poor fluidity and, hence, it is apparent that the catalyst proposed in this patent document is for use in a fixed-bed reactor and cannot be used in a fluidized-bed reactor.

Further, each of U.S. Pat. No. 3,397,153 and Examined Japanese Patent Application Publication No. Hei 2-47264 (corresponding to U.S. Pat. No. 4,590,173 and EP 0153077B) discloses a process for producing a sintered catalyst having a low density, which is prepared using a silica raw material which is a mixture of two silica sols of different average silica particle diameters. In any of these two patent documents, there is no disclosure about the data of the pore distribution of the catalyst. In the former of the two patent documents, it is intended to improve the economy of the catalyst by imparting a low density to the catalyst. In the latter of the two patent documents, it is intended to improve the mechanical strength of an oxide catalyst containing antimony, by imparting a low density to the catalyst. In these two patent documents, there are no descriptions suggesting that there is any relationship between the pore distribution of a catalyst and the yield of the desired product obtained using the catalyst, and there are no suggestions about an oxide catalyst exhibiting an improved yield of the desired product.

Any of the conventional catalysts described hereinabove is still unsatisfactory in respect of the yield of the desired product. Therefore, it has been desired to develop a catalyst which can be advantageously used in the ammoxidation of propylene, isobutene or tert-butyl alcohol in a fluidized-bed reactor, so that acrylonitrile or methacrylonitrile can be stably produced in high yield.

SUMMARY OF THE INVENTION

In this situation, the present inventors have made extensive and intensive studies with a view toward solving the above-mentioned problems of the prior art, specifically toward developing an excellent catalyst for use in the commercial production of acrylonitrile or methacrylonitrile by reacting propylene, isobutene or tert-butyl alcohol with molecular oxygen and ammonia in a fluidized-bed reactor, wherein the catalyst can produce acrylonitrile or methacrylonitrile stably in high yield. As a result, it has unexpectedly been found that, in a particulate catalyst for use in the fluidized-bed ammoxidation of propylene, isobutene or tert-butyl alcohol, when the cumulative pore volume of small-diameter pores having a pore diameter of 80 Å or less does not exceed a specific range, the catalyst exhibits a high yield of the desired product, and when the cumulative pore volume of large-diameter pores having a pore diameter of 1,000 Å or more does not exceed a specific range, the catalyst particles exhibit a high attrition resistance. Further, based on these findings, the present inventors have also found that, when the pore distribution of a catalyst is controlled so as to satisfy specific requirements, the catalyst exhibits not only a highly improved yield of the desired product, but also a high attrition resistance which renders the catalyst suitable for commercial use as a fluidized-bed catalyst. Based on these findings, the present invention has been completed.

Accordingly, it is an object of the present invention to provide a particulate porous ammoxidation catalyst for use in the production of acrylonitrile or methacrylonitrile by performing ammoxidation of propylene, isobutene or tert-butyl alcohol in a fluidized-bed reactor, wherein the catalyst exhibits not only high activity in producing the desired product, but also high attrition resistance when used on a commercial scale, so that acrylonitrile or methacrylonitrile can be obtained stably in high yield.

It is another object of the present invention to provide a method for producing the above-mentioned catalyst.

It is still another object of the present invention to provide a method for producing acrylonitrile or methacrylonitrile by using the above-mentioned catalyst.

DETAILED DESCRIPTION OF THE INVENTION

In one aspect of the present invention, there is provided a particulate porous ammoxidation catalyst for use in producing acrylonitrile or methacrylonitrile by reacting propylene, isobutene or tert-butyl alcohol with molecular oxygen and ammonia in a fluidized-bed reactor, the catalyst comprising a metal oxide and a silica carrier having supported thereon the metal oxide, wherein the silica carrier is present in an amount of from 20 to 80% by weight, based on the total weight of the metal oxide and the silica carrier and wherein the metal oxide contains at least two elements selected from the group consisting of molybdenum, bismuth, iron, vanadium, antimony, tellurium and niobium, the catalyst having a particle diameter distribution wherein the amount of catalyst particles having a particle diameter of from 5 to 200 μm is from 90 to 100% by weight, based on the weight of the catalyst, and the catalyst having a pore distribution wherein the cumulative pore volume of pores having a pore diameter of 80 Å or less is not more than 20%, based on the total pore volume of the catalyst, and the cumulative pore volume of pores having a pore diameter of 1,000 Å or more is not more than 20%, based on the total pore volume of the catalyst.

In another aspect of the present invention, there is provided a method for producing the above-mentioned catalyst, which comprises:

providing an aqueous raw material mixture containing compounds of at least two elements selected from the group consisting of molybdenum, bismuth, iron, vanadium, antimony, tellurium and niobium and containing a silica raw material, the silica raw material comprising 40 to 100% by weight of (i) at least one silica sol having an average primary silica particle diameter of from 20 to 100 nm and 60 to 0% by weight of (ii) at least one silica sol having an average primary silica particle diameter of from 5 nm to less than 20 nm, wherein the total weight of the at least one silica sol (i) and the at least one silica sol (ii) is 100% by weight, each % by weight of a silica sol being expressed in terms of the weight of silica contained in the silica sol, spray drying the aqueous raw material mixture to thereby obtain a dried catalyst precursor, and calcining the dried catalyst precursor, thereby obtaining the above-mentioned catalyst.

In still another aspect of the present invention, there is provided a method for producing acrylonitrile or methacrylonitrile, comprising reacting propylene, isobutene or tert-butyl alcohol with molecular oxygen and ammonia in a fluidized-bed reactor using the above-mentioned catalyst.

For easy understanding of the present invention, the essential features and various preferred embodiments of the present invention are enumerated below.

1. A particulate porous ammoxidation catalyst for use in producing acrylonitrile or methacrylonitrile by reacting propylene, isobutene or tert-butyl alcohol with molecular oxygen and ammonia in a fluidized-bed reactor, the catalyst comprising a metal oxide and a silica carrier having supported thereon the metal oxide, wherein the silica carrier is present in an amount of from 20 to 80% by weight, based on the total weight of the metal oxide and the silica carrier and wherein the metal oxide contains at least two elements selected from the group consisting of molybdenum, bismuth, iron, vanadium, antimony, tellurium and niobium, the catalyst having a particle diameter distribution wherein the amount of catalyst particles having a particle diameter of from 5 to 200 μm is from 90 to 100% by weight, based on the weight of the catalyst, and the catalyst having a pore distribution wherein the cumulative pore volume of pores having a pore diameter of 80 Å or less is not more than 20%, based on the total pore volume of the catalyst, and the cumulative pore volume of pores having a pore diameter of 1,000 Å or more is not more than 20%, based on the total pore volume of the catalyst.

2. The particulate porous ammoxidation catalyst according to item 1 above, wherein the metal oxide is represented by the following formula (1):

$$Mo_{12}Bi_aFe_bC_cD_dE_eF_fG_gO_n \quad (1)$$

wheerein:

C is at least one element selected from the group consisting of nickel, cobalt, manganese, zinc, magnesium, calcium, strontium and barium;

D is at least one element selected from the group consisting of chromium, tungsten, vanadium, niobium, boron, aluminum, gallium, indium, phosphorus, antimony and tellurium;

E is at least one element selected from the group consisting of rare earth elements;

F is at least one element selected from the group consisting of ruthenium, rhodium, palladium, osmium, iridium and platinum;

G is at least one element selected from the group consisting of sodium, potassium, rubidium and cesium; and a, b, c, d, e, f, g and n are, respectively, the atomic ratios of bismuth (Bi), iron (Fe), C, D, E, F, G and oxygen (O), relative to 12 atoms of molybdenum (Mo), wherein:

a is from 0.05 to 7, b is from 0.1 to 7, c is from 0 to 12, d is from 0 to 5, e is from 0 to 5, f is from 0 to 0.2, g is from 0.01 to 5, and n is the number of oxygen atoms required to satisfy the valence requirements of the other component elements present.

3. The particulate porous ammoxidation catalyst according to item 1 or 2 above, wherein the silica carrier is produced from a silica raw material comprising 40 to 100% by weight of (i) at least one silica sol having an average primary silica particle diameter of from 20 to 100 nm and 60 to 0% by weight of (ii) at least one silica sol having an average primary silica particle diameter of from 5 nm to less than 20 nm, wherein the total weight of the at least one silica sol (i) and the at least one silica sol (ii) is 100% by weight, each % by weight of a silica sol being expressed in terms of the weight of silica contained in the silica sol.

4. A method for producing the catalyst of item 1 above, which comprises:

providing an aqueous raw material mixture containing compounds of at least two elements selected from the group consisting of molybdenum, bismuth, iron, vanadium, antimony, tellurium and niobium and containing a silica raw material, the silica raw material comprising 40 to 100% by weight of (i) at least one silica sol having an average primary silica particle diameter of from 20 to 100 nm and 60 to 0% by weight of (ii) at least one silica sol having an average primary silica particle diameter of from 5 nm to less than 20 nm, wherein the total weight of the at least one silica sol (i) and the at least one silica sol (ii) is 100% by weight, each % by weight of a silica sol being expressed in terms of the weight of silica contained in the silica sol, spray drying the aqueous raw material mixture to thereby obtain a dried catalyst precursor, and calcining the dried catalyst precursor, thereby obtaining the catalyst of item 1 above.

5. The method according to item 4 above, wherein the calcination comprises a preliminary calcination and a final calcination, wherein the preliminary calcination is performed at a temperature in the range of from 150 to 430° C. and the final calcination is performed at a temperature in the range of from 450 to 750° C.

6. A method for producing acrylonitrile or methacrylonitrile, comprising reacting propylene, isobutene or tert-butyl alcohol with molecular oxygen and ammonia in a fluidized-bed reactor using the catalyst of any one of items 1 to 3 above.

7. A method for producing acrylonitrile or methacrylonitrile, comprising reacting propylene, isobutene or tert-butyl alcohol with molecular oxygen and ammonia in a fluidized-bed reactor using the catalyst produced by the method of item 4 or 5 above.

Hereinbelow, the present invention is described in detail.

The catalyst of the present invention is a particulate porous ammoxidation catalyst comprising a metal oxide and a silica carrier having supported thereon the metal oxide, wherein the silica carrier is present in an amount of from 20 to 80% by weight, based on the total weight of the metal oxide and the silica carrier and wherein the metal oxide contains at least two elements selected from the group consisting of molybdenum, bismuth, iron, vanadium, antimony, tellurium and niobium. The catalyst has a particle diameter distribution wherein the amount of catalyst particles having a particle diameter of from 5 to 200 μm is from 90 to 100% by weight, based on the weight of the catalyst, and the catalyst has also a pore distribution wherein the cumulative pore volume of pores having a pore diameter of 80 Å or less is not more than 20%, based on the total pore volume of the catalyst, and the cumulative pore volume of pores having a pore diameter of 1,000 Å or more is not more than 20%, based on the total pore volume of the catalyst.

It is preferred that, in the particulate porous ammoxidation catalyst of the present invention, the metal oxide supported on the silica carrier is represented by the following formula (1):

$$Mo_{12}Bi_aFe_bC_cD_dE_eF_fG_gO_n \quad (1)$$

wheerein:

C is at least one element selected from the group consisting of nickel, cobalt, manganese, zinc, magnesium, calcium, strontium and barium;

D is at least one element selected from the group consisting of chromium, tungsten, vanadium, niobium, boron, aluminum, gallium, indium, phosphorus, antimony and tellurium;

E is at least one element selected from the group consisting of rare earth elements;

F is at least one element selected from the group consisting of ruthenium, rhodium, palladium, osmium, iridium and platinum;

G is at least one element selected from the group consisting of sodium, potassium, rubidium and cesium; and a, b, c, d, e, f, g and n are, respectively, the atomic ratios of bismuth (Bi), iron (Fe), C, D, E, F, G and oxygen (O), relative to 12 atoms of molybdenum (Mo), wherein:
a is from 0.05 to 7,
b is from 0.1 to 7,
c is from 0 to 12,
d is from 0 to 5,
e is from 0 to 5,
f is from 0 to 0.2,
g is from 0.01 to 5, and
n is the number of oxygen atoms required to satisfy the valence requirements of the other component elements present.

In the formula (1) above, it is preferred that:

C is at least one element selected from the group consisting of nickel (Ni), cobalt (Co), zinc (Zn), manganese (Mn) and magnesium (Mg);

E is at least one element selected from the group consisting of lanthanum (La), cerium (Ce), praseodymium (Pr) and neodymium (Nd);

G is at least one element selected from the group consisting of potassium (K), rubidium (Rb) and cesium (Cs); and the following conditions are satisfied:
a is from 0.1 to 3,
b is from 0.1 to 3,
c is from 5 to 10,
e is from 0.05 to 2, and
g is from 0.05 to 1.0.

Further, when the metal oxide in the catalyst of the present invention is represented by the formula (1) above, it is more preferred that the metal oxide is represented by the following formula (2) or (3).

$$Mo_{12}(Bi_{1-i}Ce_i)_k Fe_l Ni_m Q_q R_r O_n \qquad (2)$$

wherein:

Mo, Bi, Ce, Fe and Ni represent molybdenum, bismuth, cerium, iron and nickel, respectively;

Q is at least one element selected from the group consisting of magnesium and zinc;

R is at least one element selected from the group consisting of potassium, rubidium and cesium; and k, l, m, q, r and n are, respectively, the atomic ratios of the total of bismuth (Bi) and cerium (Ce), iron (Fe), nickel (Ni), Q, R and oxygen (O), relative to 12 atoms of molybdenum (Mo), wherein:
k=0.5 to 2,
l=0.1 to 3,
m=4 to 10,
q=0 to 3,
r=0.01 to 0.5,
i=0.6 to 0.8, wherein i is the atomic ratio of cerium, relative to the total of bismuth and cerium, and
n is the number of oxygen atoms required to satisfy the valence requirements of the other component elements present.

$$Mo_{12}Bi_h Fe_p Ni_s T_t R_r X_x O_n \qquad (3)$$

wherein:

Mo, Bi, Fe and Ni represent molybdenum, bismuth, iron and nickel, respectively;

T is at least one element selected from the group consisting of chromium and indium;

R is at least one element selected from the group consisting of potassium, rubidium and cesium;

X is at least one element selected from the group consisting of manganese, magnesium, zinc, cerium, sodium and phosphorus; and h, p, s, t, r, x and n are, respectively, the atomic ratios of bismuth (Bi), iron (Fe), nickel (Ni), T, R. X and oxygen (O), relative to 12 atoms of molybdenum (Mo), wherein:
h=0.1 to 3,
p=0.1 to 3,
s=4 to 10,
t=0.1 to 2,
r=0.01 to 0.5,
x=0 to 3, and
n is the number of oxygen atoms required to satisfy the valence requirements of the other component elements present.

The catalyst of the present invention has a particle diameter distribution wherein the amount of catalyst particles having a particle diameter of from 5 to 200 µm is from 90 to 100% by weight, based on the weight of the catalyst. When the amount of catalyst particles having a particle diameter of from 5 to 200 µm is less than 90% by weight, based on the weight of the catalyst, there is a problem in that the amount of small-diameter catalyst particles having a particle diameter of less than 5 µm and the amount of large-diameter catalyst particles having a particle diameter of larger than 200 µm become too large, rendering poor the fluidity of the catalyst and hence leading to poor results of the reaction.

With respect to the pore distribution of the catalyst of the present invention, the catalyst has a pore distribution wherein the cumulative pore volume of pores having a pore diameter of 80 Å or less is not more than 20%, based on the total pore volume of the catalyst, and the cumulative pore volume of pores having a pore diameter of 1,000 Å or more is not more than 20%, based on the total pore volume of the catalyst.

It is more preferred that the catalyst has a pore distribution wherein the cumulative pore volume of pores having a pore diameter of 80 Å or less is not more than 15%, more advantageously not more than 10%, based on the total pore volume of the catalyst. Also, it is more preferred that the cumulative pore volume of pores having a pore diameter of 1,000 Å or more is not more than 15%, more advantageously not more than 10%, based on the total pore volume of the catalyst.

When the cumulative pore volume of pores having a pore diameter of 80 Å or less is more than 20%, based on the total pore volume of the catalyst, the catalyst poses a problem in that the yield of the desired product (i.e., acrylonitrile or methacrylonitrile) becomes low. On the other hand, when the cumulative pore volume of pores having a pore diameter of 1,000 Å or more is more than 20%, based on the total pore volume of the catalyst, a problem arises in that the attrition resistance of the catalyst becomes poor and, hence, the catalyst cannot exhibit a satisfactorily high attrition resistance which renders the catalyst suitable for commercial use, so that it becomes impossible to stably produce the desired product. The reason why the yield of the desired product becomes low when the cumulative pore volume of pores having a pore diameter of 80 Å or less is more than 20%, based on the total pore volume of the catalyst, has not yet been elucidated. However, it is presumed that, in the small-diameter pores having a pore diameter of 80 Å or less, the residence time of the reaction product in the pores of the catalyst becomes too long, thus accelerating decomposition of the reaction product, leading to a lowering of the yield of the desired product.

With respect to the method for measuring the pore distribution of a catalyst, there are known conventional methods, such as the gas adsorption method and the mercury porosimetry; however, the results of measuring are different from method to method. In the present invention, the measurement of the pore distribution of the catalyst is performed by the mercury porosimetry using "Auto Pore-9200" (trade name; manufactured and sold by Shimadzu Corporation, Japan). The mercury porosimetry means a method in which an external pressure is applied to force mercury into the pores in the catalyst, the amount of mercury forced into the pores is recorded in terms of a function of the pressure applied, and, based on this record, the pore distribution of the catalyst is obtained. In the calculation for obtaining the pore distribution of the catalyst, it is assumed that pores have a cylindrical shape. A cumulative pore volume with respect to the pore diameters measured is obtained by the mercury porosimetry and plotted to obtain a cumulative pore distribution curve which is used as primary data. The cumulative pore distribution curve relative to the pore diameters measured is differentiated with the pore diameter to obtain a differential pore distribution. The differential pore distribution is plotted against the pore diameter, to thereby obtain a differential pore distribution curve, which is the so-called pore distribution. Specifically, the measurement of the pore distribution is performed as follows. 0.3 to 0.4 g of a specimen (of the catalyst) is charged into a dilatometer, and the dilatometer is degassed using a vacuum pump so that the internal pressure of the dilatometer becomes 6.67 Pa or less. Subsequently, mercury is charged into the dilatometer. Then, the dilatometer containing the specimen and mercury is placed in an autoclave. In the autoclave, the external pressure of the dilatometer is gradually increased from atmospheric pressure to 413 MPa. The level of the mercury in the dilatometer is tracked and recorded as it becomes lowered under pressure. The pore distribution is measured from the changes in the level of mercury (namely, from the changes in amount of mercury forced into the pores of the catalyst) in terms of a function of the pressure applied.

In the present invention, when performing the measurement of the pore distribution of the catalyst by the mercury porosimetry method, the interstices between the catalyst particles are measured as pores having a pore diameter in the range of from tens of thousands to hundreds of thousands Å. Therefore, in the present invention, the term "total pore volume" means the cumulative pore volume of pores having a pore diameter of 5,000 Å or less.

In the cumulative pore distribution curve relative to the pore diameters measured, as obtained by the above-mentioned mercury porosimetry, the cumulative pore volume of pores having a pore diameter of 80 Å or less is calculated as the cumulative pore volume of pores having a pore diameter in the range of from the lower limit of measurement (about 30 Å) to 80 Å, and the cumulative pore volume of pores having a pore diameter of 1,000 Å or more is calculated as the cumulative pore volume of pores having a pore diameter in the range of from 1,000 to 5,000 Å. Therefore, the total pore volume is calculated as the cumulative pore volume of pores having a pore diameter in the range of from the lower limit of measurement to 5,000 Å.

With respect to the measures for controlling the pore distribution of the catalyst of the present invention, the pore distribution can be controlled by, for example, any of the following methods: a method in which there is changed the particle diameter of a silica sol as a silica raw material (i.e., the average primary silica particle diameter); a method in which the ratios of the silica carrier and metal oxide present in the catalyst are changed; a method in which the calcination temperature is changed; a method in which a fumed silica is used as a part of the silica raw material; and a method in which the below-mentioned aqueous slurry of raw materials of the catalyst (i.e., aqueous raw material mixture) is provided so as to contain a fine particulate substance which is decomposable when burnt in air at a temperature which is equal to or lower than the calcination temperature, and the slurry is subjected to a spray drying and a calcination. In the case of the method in which the pore distribution of the catalyst is controlled by changing the ratios of the silica carrier and metal oxide present in the catalyst, when the ratio of the metal oxide is increased, the pore distribution of the catalyst is shifted so that the ratio of large-diameter pores is increased. In the case of the method in which the pore distribution of the catalyst is controlled by changing the calcination temperature, when the calcination temperature is increased, the pore distribution of the catalyst is shifted so that the ratio of large-diameter pores is increased. Further, in the case of the method in which the pore distribution of the catalyst is controlled by using an aqueous slurry of raw materials of the catalyst (i.e., aqueous raw material mixture) containing a fine particulate substance which is decomposable when burnt in air at a temperature which is equal to or lower than the calcination temperature, the fine particulate substance forms voids when being burnt and decomposed, and the voids are left as pores of the catalyst. Therefore, it is preferred that the fine particulate substance contained in the aqueous raw material mixture has a size in the range of from 100 to 1,000 Å, more advantageously 200 to 500 Å, and that the fine particulate substance is made of an organic material which does not leave a residue after being burnt. (As examples of such fine particulate substances, there can be mentioned a sol of a crystalline cellulose having excellent dispersibility in water and a microemulsion of polystyrene). With respect to each of the method for controlling the pore distribution by changing the particle diameter of the silica sol as a silica raw material (i.e., the average primary silica particle diameter) and the method for controlling the pore distribution by employing a fumed silica as a part of the silica raw material, explanations are made below in connection with the method for producing the catalyst of the present invention. It should be noted that the measures for satisfying the requirements concerning the physical structure (i.e., the pore distribution) of the catalyst of the present invention are not limited to the aforementioned examples of methods, but any measures can be employed as long as the requirements concerning the physical structure (i.e., the pore distribution) of the catalyst of the present invention are satisfied.

Generally, it is important that a catalyst exhibit satisfactorily high attrition resistance which renders the catalyst suitable for commercial use. In the present invention, the measurement of the attrition resistance of the catalyst is performed in accordance with the method described in "Test Method for Synthetic Fluid Cracking Catalyst" (American Cyanamid Co., Ltd. 6/31-4m-1/57) (hereinafter referred simply as "ACC method"), which is generally known as a method for determining the attrition resistance of a fluidized-bed catalyst for use in the catalytic cracking. The attrition resistance of the catalyst of the present invention is measured in terms of the attrition loss which is defined by the following formula:

$$\text{attrition loss (\%)} = B/(C-A) \times 100$$

wherein:

A is the weight (g) of the catalyst which is lost by attrition in the period of from 0 hour point to 5 hour point after the start of the attrition resistance test;

B is, according to the ordinary ACC method, the weight (g) of the catalyst which is lost by attrition in the period of from 5 hour point to 20 hour point after the start of the attrition resistance test; however, in the present invention, this B is defined as the weight (g) of the catalyst which is lost by attrition in the period of from 5 hour point to 120 hour point after the start of the attrition resistance test; and C is the weight (g) of the catalyst used in the attrition resistance test.

When the catalyst exhibits an attrition loss of 7% or less, it is judged that the catalyst has a satisfactorily high attrition resistance which renders the catalyst suitable for commercial use.

In the catalyst of the present invention, silica is used as the carrier having supported thereon the metal oxide. Silica is inherently inert, differing from other carrier materials, and can serve as an excellent binder for the ingredients of the metal oxide without impairing the selectivity of the catalyst for the desired product and serve to impart a high attrition resistance to the catalyst. Thus, silica is suitable for use as the carrier in the catalyst of the present invention. The amount of silica carrier is in the range of from 20 to 80% by weight, preferably from 30 to 70% by weight, more preferably from 40 to 60% by weight, based on the total weight of the metal oxide and the silica carrier.

With respect to the raw material for producing the carrier to support thereon the metal oxide in the catalyst of the present invention, oxide sols, such as a titania sol, a zirconia sol and a tin oxide sol, may be used in combination with a silica sol. When such oxide sol(s) other than a silica sol is used in combination with a silica sol, the amount of oxide sol(s) other than a silica sol in terms of the oxide is preferably 10% by weight or less, more preferably 5% by weight or less, based on the weight of the carrier in the catalyst.

As an impurity in the silica sol used as the silica raw material for producing the catalyst of the present invention, there can be mentioned aluminum. The atomic ratio of aluminum present as an impurity in the silica sol is preferably 0.04 or less, more preferably 0.02 or less, relative to 100 atoms of silicon present in the silica sol. The aluminum content of the silica sol may be zero; however, even when the atomic ratio of aluminum present in the silica sol is much less than 0.02, relative to 100 atoms of silicon present in the silica sol, no further improvement can be achieved in the performance of the catalyst, as compared to the case where the atomic ratio of aluminum present as an impurity in the silica sol is 0.02, relative to 100 atoms of silicon present in the silica sol. Various methods are known for producing a silica sol of very high purity, which is for use in various application fields, such as the fields of an abrasive for polishing the surface of a semiconductor, a raw material for a quartz fiber, and a carrier for a catalyst. For example, methods for producing a high purity silica sol containing only an extremely small amount of aluminum as an impurity are disclosed in Unexamined Japanese Patent Application Laid-Open Specification Nos. Sho 60-127216, Sho 61-158810, Sho 63-285112, Hei 4-231319 and Hei 5-85718, and Examined Japanese Patent Application Publication No. Sho 55-10534. The amount of aluminum present as an impurity in a silica sol can be measured by the ICP (inductively coupled plasma) emission spectroscopy.

When it is intended to satisfy the physical structure requirements (pore distribution) of the catalyst of the present invention by changing the particle diameter of the silica sol as the silica raw material (i.e., the average primary silica particle diameter), it is especially effective to produce the silica carrier from a silica raw material comprising 40 to 100% by weight of (i) at least one silica sol having an average primary silica particle diameter of from 20 to 100 nm and 60 to 0% by weight of (ii) at least one silica sol having an average primary silica particle diameter of from 5 nm to less than 20 nm, wherein the total weight of the at least one silica sol (i) and the at least one silica sol (ii) is 100% by weight, each % by weight of a silica sol being expressed in terms of the weight of silica contained in the silica sol. When the at least one silica sol (i) has an average primary silica particle diameter of from 20 nm to less than 40 nm, the amount of at least one silica sol (i) is preferably in the range of from 80 to 100% by weight, based on the total weight of the at least one silica sol (i) and the at least one silica sol (ii), each % by weight of a silica sol being expressed in terms of the weight of silica contained in the silica sol. When the at least one silica sol (i) has an average primary silica particle diameter of from 40 nm to less than 60 nm, the amount of at least one silica sol (i) is preferably in the range of from 60% by weight to less than 80% by weight, based on the total weight of the at least one silica sol (i) and the at least one silica sol (ii), each % by weight of a silica sol being expressed in terms of the weight of silica contained in the silica sol. When the at least one silica sol (i) has an average primary silica particle diameter of from 60 to 100 nm, the amount of at least one silica sol (i) is preferably in the range of from 40% by weight to less than 60% by weight, based on the total weight of the at least one silica sol (i) and the at least one silica sol (ii), each % by weight of a silica sol being expressed in terms of the weight of silica contained in the silica sol. With respect to the at least one silica sol (ii) (having an average primary silica particle diameter of from 5 nm to less than 20 nm), the average primary silica particle diameter is preferably in the range of from 7 to 15 nm.

On the other hand, when it is intended to satisfy the physical structure requirements (pore distribution) of the catalyst of the present invention by employing a fumed silica as a part of the silica raw material, it is preferred that a fumed silica having an average primary silica particle diameter of from 5 to 30 nm is used in an amount of from 10 to 50% by weight, based on the weight of the silica carrier present in the catalyst of the present invention. The average primary silica particle diameter of the fumed silica is more preferably in the range of from 10 to 20 nm. The amount of fumed silica is more preferably in the range of from 20 to 40% by weight, based on the weight of the silica carrier present in the catalyst of the present invention.

The average primary silica particle diameter of the silica sol or fumed silica can be measured by a conventional method, such as the BET method or the electron microscopy. In the present invention, the average primary silica particle diameter of the silica sol or fumed silica is measured by the BET method, namely the method based on the BET adsorption isotherm (i.e., the Brunauer-Emmett-Teller adsorption isotherm). Specifically, in the measurement of the average primary silica particle diameter of a silica sol, the silica sol is heated at a temperature in the range of from 100 to 200° C. so as to evaporate the water as the dispersion medium of the silica sol, to thereby obtain silica particles. The obtained silica particles are caused to adsorb nitrogen gas to saturation at the temperature of a liquid nitrogen, and then the temperature of the resultant nitrogen gas-adsorbed silica particles is elevated to room temperature, to thereby cause desorption of nitrogen gas from the silica particles. The amount of desorbed nitrogen gas is measured. From the measured amount of desorbed nitrogen gas, the specific surface area (S) (m²/g) of the particles is calculated. For calculation of the average primary silica particle diameter, it is assumed that all primary silica particles are spherical and have the same diameter (D) (nm) and that the specific gravity (ρ) of the silica particles (i.e., amorphous silica) present in the silica sol is 2.2. The silica particle diameter (D) (nm) can be calculated by the below-mentioned formulae (wherein n represents the number of primary silica particles per g of primary silica particles):

$$\rho = 4/3 \times \pi \times (D \times 10^{-7}/2)^3 \times n,$$

$$S = 4 \times \pi \times (D \times 10^{-9}/2)^2 \times n,$$

and therefore, $$D = 6,000 \times \rho/S.$$

A most effective measure for controlling the pore distribution of a catalyst to satisfy the physical structure requirements of the catalyst of the present invention, is a method in which there is changed the particle diameter of the silica sol as a silica raw material (i.e., the average primary silica particle diameter). Generally, when the diameter of the silica particles of a silica sol used for producing a catalyst is increased, the strength of the catalyst tends to be lowered. However, it is desired that a commercial catalyst for use in a fluidized-bed reactor exhibits high strength. Therefore, conventionally, there has been generally used, as a silica raw material, a silica sol having an average primary silica particle diameter of 10-odd nm. When such silica sol is used as a silica raw material for producing a silica carrier, a problem arises in that the cumulative pore volume of pores having a pore diameter of 80 Å or less becomes more than 20%, based on the total pore volume of the resultant catalyst and, hence, the catalyst does not satisfy the physical structure requirements of the catalyst of the present invention. On the other hand, when only one silica sol is used as a silica raw material for producing a silica carrier, a problem arises in that, in a case where the average primary silica particle diameter is relatively small, the cumulative pore volume of pores having a pore diameter of 80 Å or less is likely to be more than 20%, based on the total pore volume of the resultant catalyst. In addition, when only one silica sol is used as a silica raw material for producing a silica carrier, another problem arises in that, in a case where the average primary silica particle diameter is relatively large, the cumulative pore volume of pores having a pore diameter of 1,000 Å or more is likely to be more than 20%, based on the total pore volume of the resultant catalyst. That is, the physical structure requirements of the catalyst of the present invention cannot be easily satisfied in the absence of the knowledge of the present invention. Therefore, by using the methods disclosed in the prior art documents, it is substantially impossible to obtain a catalyst which satisfies the physical structure requirements of the catalyst of the present invention.

Hereinbelow, explanations are made in detail on the method for producing the catalyst of the present invention.

The catalyst of the present invention can be efficiently produced by, for example, a method for producing the catalyst of the present invention, which comprises:

providing an aqueous raw material mixture containing compounds of at least two elements selected from the group consisting of molybdenum, bismuth, iron, vanadium, antimony, tellurium and niobium and containing a silica raw material, the silica raw material comprising 40 to 100% by weight of (i) at least one silica sol having an average primary silica particle diameter of from 20 to 100 nm and 60 to 0% by weight of (ii) at least one silica sol having an average primary silica particle diameter of from 5 nm to less than 20 nm, wherein the total weight of the at least one silica sol (i) and the at least one silica sol (ii) is 100% by weight, each % by weight of a silica sol being expressed in terms of the weight of silica contained in the silica sol, spray drying the aqueous raw material mixture to thereby obtain a dried catalyst precursor, and calcining the dried catalyst precursor, thereby obtaining the catalyst of the present invention.

This method for producing the catalyst of the present invention is described in detail. The method for producing the catalyst of the present invention comprises the following steps: step (1) of providing an aqueous raw material mixture (i.e., aqueous raw material mixture preparation step), step (2) of spray drying the aqueous raw material mixture to thereby obtain a dried catalyst precursor (i.e., drying step), and step (3) of calcining the dried catalyst precursor (i.e., calcination step). These steps are described hereinbelow in detail.

Step (1) (Aqueous Raw Material Mixture Preparation Step)

In step (1), an aqueous slurry of raw materials of the catalyst (i.e., aqueous raw material mixture) is prepared. In the raw materials, each of the elements (which are to be incorporated into the catalyst), such as molybdenum, bismuth, iron, nickel, cobalt, manganese, zinc, magnesium, calcium, strontium, barium, chromium, tungsten, vanadium, niobium, boron, aluminum, gallium, indium, at least one rare earth element, phosphorus, antimony, tellurium, sodium, potassium, rubidium and cesium, may be present in the form of an ammonium salt, a nitrate, a chloride, a sulfate, an organic acid salt and/or an inorganic acid, which are soluble in water or nitric acid. Especially, it is preferred that each of molybdenum, tungsten and vanadium is used in the form of an ammonium salt; that each of bismuth, iron, nickel, cobalt, manganese, zinc, magnesium, calcium, strontium, barium, chromium, aluminum, gallium, indium, at least one rare earth element, sodium, potassium, rubidium and cesium, is used in the form of a nitrate; and that each of niobium, boron, phosphorus and tellurium is used in the form of an inorganic acid. Further, with respect to the source of antimony used as a raw material of the catalyst, an antimony oxide can be advantageously used.

Of these raw materials of the catalyst, with respect to those raw materials having poor solubility in water (e.g., sources of antimony and niobium), it is preferred that, prior to use, these raw materials are dissolved in water in the presence of a water-soluble chelating agent, such as citric acid, oxalic acid, tartaric acid or hydrogen peroxide.

With respect to niobic acid, which has poor solubility in water, it is preferred to improve the solubility of niobic acid by the method as described in Unexamined Japanese Patent Application Laid-Open Specification No. Hei 11-47598; specifically, it is preferred to use niobic acid in the form of a niobic acid-containing aqueous mixture which contains niobic acid, a dicarboxylic acid (e.g. oxalic acid) and ammonia, wherein the molar ratio (dicarboxylic acid/Nb molar ratio) of the dicarboxylic acid to the niobic acid in terms of niobium is in the range of from 1 to 4 and the molar ratio (ammonia/Nb molar ratio) of the ammonia to the niobic acid in terms of niobium is 2 or less.

Diantimony trioxide has poor solubility in water. However, diantimony trioxide can be dissolved in water by a method in which a mixture of diantimony trioxide and ammonium metavanadate or a mixture of diantimony trioxide, ammonium metavanadate and ammonium paramolybdate, is added to water, and the resultant aqueous mixture is heated at a temperature in the range of from 80° C. to the boiling point (the boiling point is generally about 100° C.) to thereby obtain an aqueous solution.

The silica raw material used in the method of the present invention for producing the catalyst of the present invention is a silica raw material comprising 40 to 100% by weight of (i) at least one silica sol having an average primary silica particle diameter of from 20 to 100 nm and 60 to 0% by weight of (ii) at least one silica sol having an average primary silica particle diameter of from 5 nm to less than 20 nm, wherein the total weight of the at least one silica sol (i) and the at least one silica sol (ii) is 100% by weight, each % by weight of a silica sol being expressed in terms of the weight of silica contained in the silica sol.

The aqueous slurry of raw materials of the catalyst (i.e., aqueous raw material mixture) can be prepared, for example, as follows. Aqueous solutions of ammonium salts of molybdenum, tungsten and the like are added to a silica sol (which is a silica raw material) to obtain a silica sol-containing aqueous mixture. On the other hand, nitrates of other component elements (i.e., bismuth, iron, nickel, cobalt, manganese, zinc, magnesium, calcium, strontium, barium, chromium, aluminum, gallium, indium, at least one rare earth element, sodium, potassium, rubidium and cesium) are dissolved in water or aqueous nitric acid. The resultant aqueous solution is added to the above-mentioned silica sol-containing aqueous mixture. When a fumed silica is employed as a part of the silica raw material, or it is intended to prepare a phosphorus-containing catalyst, an aqueous raw material mixture is prepared as follows. An aqueous suspension of fumed silica is added to a silica sol to obtain an aqueous silica mixture, and then phosphoric acid is added to the aqueous silica mixture, followed by addition of sources of other component elements, to thereby obtain an aqueous raw material mixture. The order of mixing of the raw materials may be changed.

With respect to the sources of component elements, which have poor solubility in water, these sources can be used after appropriately performing the above-mentioned treatment for improving the solubility thereof.

Step (2) (Drying Step)

In step (2), the aqueous raw material mixture obtained in step (1) above is subjected to spray drying, to thereby obtain spherical dried particles (i.e., a dried catalyst precursor). The spray drying of the aqueous raw material mixture can be conducted by a conventional method generally employed in the commercial production of a catalyst. Examples of such methods include a centrifugation method, a two-phase flow nozzle method and a high pressure nozzle method. Of these, a centrifugation method is especially preferred. With respect to a heat source for drying, it is preferred to use air which has been heated by steam, an electric heater or the like. The temperature of the spray dryer at an inlet thereof is from 100 to 400° C., preferably from 150 to 300° C., and the temperature of the spray dryer at an outlet thereof is from 100 to 170° C., preferably from 120 to 150° C.

Step (3) (Calcination Step)

In step (3), the dried particles (i.e., a dried catalyst precursor) obtained in step (2) above are calcined to thereby obtain a desired catalyst. If desired, the dried catalyst precursor may be first subjected to a preliminary calcination (which is optional) in an oxygen-containing atmosphere (e.g., air) at a temperature of from 150 to 430° C. for 30 minutes to 10 hours, before performing a final calcination in an oxygen-containing atmosphere (e.g., air) at a temperature in the range of from 450 to 750° C., preferably from 500 to 700° C., for 1 to 20 hours. The preliminary calcination is optionally performed for the purpose of burning ammonium nitrates derived from the ammonium salts and nitrates used as raw materials for the catalyst. In the preliminary calcination, if explosive burning of ammonium nitrates occurs, problems may be caused in that a distortion or cracking of the catalyst occurs, thus impairing the fluidity and attrition resistance of the catalyst. Therefore, burning of ammonium nitrates is performed slowly at a relatively low temperature. For the calcination, a kiln, such as a rotary kiln, a tunnel kiln or a muffle kiln, can be used.

Hereinbelow, an explanation is made with respect to the measurement of the particle diameter distribution of the thus obtained catalyst. The "particle diameter distribution" is data of the weight percentages of groups of catalyst particles wherein the groups respectively have different specific ranges of particle diameter, based on the weight of the catalyst. In the present invention, the measurement of the particle diameter distribution is performed by the following method. A sieve having a mesh size of 200 μm (manufactured and sold by Buckbee-Mears, U.S.A.) (upper sieve) is placed on a sieve having a mesh size of 5 μm (manufactured and sold by Buckbee-Mears, U.S.A.) (lower sieve), and a receiver is provided under the lower sieve having a mesh size of 5 μm. A specimen of the catalyst particles is introduced onto the upper sieve, and the upper and lower sieves are shaken, thereby effecting a screening of the catalyst particles. The catalyst particles which remained on the lower sieve (having a mesh size of 5 μm) are taken out and weighed. The thus obtained weight of the catalyst particles which remained on the lower sieve is divided by the weight of the catalyst particles introduced onto the upper sieve, and the resultant quotient is multiplied by 100. The resultant product is obtained as the amount (% by weight) of catalyst particles having a particle diameter of from 5 to 200 μm, based on the weight of the catalyst. In the present invention, the amount of catalyst particles having a particle diameter of from 5 to 200 μm is in the range of from 90 to 100% by weight, based on the weight of the catalyst.

The excellent catalyst of the present invention can be produced by the simple method as described hereinabove. The thus obtained catalyst of the present invention can be used for producing acrylonitrile or methacrylonitrile by reacting propylene, isobutene or tert-butyl alcohol with molecular oxygen and ammonia. The above-mentioned ammoxidation reaction is conducted in a fluidized-bed reactor. Propylene, isobutene, tert-butyl alcohol and ammonia used in the present invention need not be of a very high purity but may be of a commercial grade. As a source of molecular oxygen, air is usually preferred. Gas having an increased oxygen content such as a gaseous mixture of air and oxygen, is also usable. In the ammoxidation reaction, the molar ratios of propylene, isobutene or tert-butyl alcohol:ammonia:molecular oxygen used as gaseous raw materials for the ammoxidation are generally in the range of 1:0.8 to 1.4:1.4 to 2.4, preferably 1:0.9 to 1.3:1.6 to 2.2. The reaction temperature may be from 350 to 550° C., preferably from 400 to 500° C. The reaction may usually be conducted under a pressure of from atmospheric pressure to 0.3 MPa. The time of contact (contact time) between a gaseous mixture of raw materials and the catalyst may be from 0.5 to 20 (sec·g/cc), preferably from 1 to 10 (sec·g/cc).

In the present invention, the contact time is defined by the following formula:

contact time (sec·g/cc)=$(W/F) \times 273/(273+T) \times P/0.10$ wherein:

W represents the weight (g) of the catalyst,

F represents the flow rate (Ncc/sec) of the gaseous raw material mixture in the normal state (0° C., 1 atm), T represents the reaction temperature (° C.), and P represents the reaction pressure (MPa).

BEST MODE FOR CARRYING OUT THE INVENTION

Hereinbelow, the present invention will be described in more detail with reference to the following Examples and Comparative Examples, which should not be construed as limiting the scope of the present invention.

In the following Examples and Comparative Examples, the particle diameter distribution of a catalyst was measured using a sieve. Specifically, the measurement of the particle diameter distribution was performed by the following method. A sieve having a mesh size of 200 μm (manufactured and sold by Buckbee-Mears, U.S.A.) (upper sieve) was placed on a sieve having a mesh size of 5 μm (manufactured and sold by Buckbee-Mears, U.S.A.) (lower sieve), and a receiver was provided under the lower sieve having a mesh size of 5 μm. A specimen of the catalyst particles was introduced onto the upper sieve, and the upper and lower sieves were shaken, thereby effecting a screening of the catalyst particles. The catalyst particles which remained on the lower sieve (having a mesh size of 5 μm) were taken out and weighed. The thus obtained weight of the catalyst particles which remained on the lower sieve was divided by the weight of the catalyst particles introduced onto the upper sieve, and the resultant quotient was multiplied by 100. The resultant product was obtained as the amount (% by weight) of catalyst particles having a particle diameter of from 5 to 200 μm, based on the weight of the catalyst. It was found that, with respect to all catalysts obtained in the Examples and Comparative Examples, the amount of catalyst particles having a particle diameter of from 5 to 200 μm was 100% by weight, based on the weight of the catalyst.

In the Examples and Comparative Examples, the conversion and yield used for evaluating the results of the reaction are defined as follows:

Conversion (%)=(mole of propylene reacted)/(mole of propylene fed)×100

Yield of acrylonitrile (%)=(mole of acrylonitrile formed)/(mole of propylene fed)×100

A Pyrex glass fluidized-bed reactor tube having an inner diameter of 25 mm was used as a reaction apparatus. The reaction pressure (P) was maintained at 0.15 MPa, and the amount (W) of a catalyst charged in the reactor was 40 to 60 g. The flow rate (F) of a gaseous raw material mixture introduced into the reactor was 250 to 450 Ncc/sec (in terms of the value as measured in the normal state (0° C., 1 atm)), and the reaction temperature (T) was maintained at 430° C.

In the present invention, the contact time is defined by the following formula:

contact time(sec·g/cc)=($W/F$)×273/(273+$T$)×P/0.10 wherein:

W represents the weight (g) of the catalyst, represents the flow rate (Ncc/sec) of the gaseous raw material mixture in the normal state (0° C., 1 atm), T represents the reaction temperature (° C.), and P represents the reaction pressure (MPa).

The composition of the gaseous raw material mixture introduced into the reactor was as follows:

propylene/ammonia/air=1/1.25/8.0 to 10.0 (1.6 to 2.0 in terms of molecular oxygen).

For the evaluation of the attrition resistance of the catalysts obtained in the Examples and Comparative Examples, the attrition loss of each of the catalysts was measured in accordance with the ACC method. The attrition loss is defined by the following formula:

attrition loss (%)=$B/(C-A)$×100 wherein:

A is the weight (g) of the catalyst which is lost by attrition in the period of from 0 hour point to 5 hour point after the start of the attrition resistance test;

B is the weight (g) of the catalyst which is lost by attrition in the period of from 5 hour point to 120 hour point after the start of the attrition resistance test; and C is the weight (g) of the catalyst used in the attrition resistance test.

When the catalyst exhibits an attrition loss of 7% or less, it is judged that the catalyst has a satisfactorily high attrition resistance which renders the catalyst suitable for commercial use.

EXAMPLE 1

An ammoxidation catalyst comprised of a metal oxide supported on a silica carrier which was present in an amount of 50% by weight, based on the total weight of the metal oxide and the silica carrier, wherein the metal oxide had a metal composition represented by the formula:

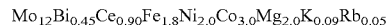

$Mo_{12}Bi_{0.45}Ce_{0.90}Fe_{1.8}Ni_{2.0}Co_{3.0}Mg_{2.0}K_{0.09}Rb_{0.05}$ was prepared as follows.

42.2 g of bismuth nitrate [$Bi(NO_3)_3 \cdot 5H_2O$], 75.5 g of cerium nitrate [$Ce/(NO_3)_3 \cdot 6H_2O$], 140.5 g of iron nitrate [$Fe(NO_3)_3 \cdot 9H_2O$], 112.4 g of nickel nitrate [$Ni(NO_3)_2 \cdot 6H_2O$], 168.8 g of cobalt nitrate [$Co(NO_3)_2 \cdot 6H_2O$], 99.1 g of magnesium nitrate [$Mg(NO_3)_2 \cdot 6H_2O$], 1.76 g of potassium nitrate [$KNO_3$] and 1.43 g of rubidium nitrate [$RbNO_3$] were dissolved in 405.3 g of a 16.6% by weight aqueous nitric acid solution. The resultant solution was added to 1,666.7 g of an aqueous silica sol having an $SiO_2$ content of 30% by weight and an average primary silica particle diameter of 22 nm, to obtain a mixture. To the thus obtained mixture was added a solution of 409.4 g of ammonium paramolybdate [$(NH_4)_6Mo_7O_{24} \cdot 4H_2O$] in 824.7 g of water, to thereby obtain an aqueous raw material mixture. The thus obtained aqueous raw material mixture was fed to a parallel flow type spray-drying apparatus, in which the aqueous raw material mixture was atomized by means of a sprayer having a dish type rotor disposed above the central portion of a dryer of the spray-drying apparatus, and dried while maintaining the inlet temperature of the dryer at about 250° C. and the outlet temperature of the dryer at about 140° C., to thereby obtain particles (i.e., a dried catalyst precursor). The dried catalyst precursor was subjected to a preliminary calcination in air in an electric kiln at 350° C. for 1 hour and then subjected to a final calcination in air at 580° C. for 2 hours, thereby obtaining a catalyst.

With respect to the obtained catalyst, a measurement of the pore distribution was performed. As a result, it was found that the cumulative pore volume of pores having a pore diameter of 80 Å or less was 0.005 cc/g, the cumulative pore volume of pores having a pore diameter of 1,000 Å or more was 0.012 cc/g, and the total pore volume of the catalyst was 0.232 cc/g. That is, the cumulative pore volume of pores having a pore diameter of 80 Å or less was 2.2%, and the cumulative pore volume of pores having a pore diameter of 1,000 Å or more was 5.2%, each based on the total pore volume of the catalyst.

Using 50 g of the obtained catalyst, an ammoxidation reaction of propylene was conducted. The contact time in the ammoxidation reaction was 4.3 (sec·g/cc). Results of the reaction were evaluated 24 hours after the start of the reaction. As a result, it was found that the conversion of propylene was 99.0%, and the yield of acrylonitrile was 84.0%.

50 g of the obtained catalyst was subjected to an attrition resistance test in accordance with the ACC method. As a result, the catalyst exhibited an attrition loss (%) of 5.7%. The composition of the catalyst and the production conditions for the catalyst are shown in Table 1. The pore distribution and attrition resistance (in terms of the attrition loss (%)) of the catalyst, and the results of the ammoxidation reaction are shown in Table 2.

COMPARATIVE EXAMPLE 1

An ammoxidation catalyst was prepared in substantially the same manner as in Example 1, except that 1,666.7 g of an aqueous silica sol having an $SiO_2$ content of 30% by weight and an average primary silica particle diameter of 12 nm was used alone as a silica raw material and that the final calcination temperature was 590° C.

With respect to the obtained catalyst, a measurement of the pore distribution was performed. As a result, it was found that the cumulative pore volume of pores having a pore diameter of 80 Å or less was 0.058 cc/g, the cumulative pore volume of pores having a pore diameter of 1,000 Å or more was 0.001 cc/g, and the total pore volume of the catalyst was 0.220 cc/g. That is, the cumulative pore volume of pores having a pore diameter of 80 Å or less was 26.4%, and the cumulative pore volume of pores having a pore diameter of 1,000 Å or more was 0.5%, each based on the total pore volume of the catalyst.

Using 50 g of the obtained catalyst, an ammoxidation reaction of propylene was conducted. The contact time in the ammoxidation reaction was 3.7 (sec·g/cc). Results of the reaction were evaluated 24 hours after the start of the reaction. As a result, it was found that the conversion of propylene was 99.1%, and the yield of acrylonitrile was 82.4%.

50 g of the obtained catalyst was subjected to an attrition resistance test in accordance with the ACC method. As a result, the catalyst exhibited an attrition loss (%) of 2.9%. The composition of the catalyst and the production conditions for the catalyst are shown in Table 1. The pore distribution and attrition resistance (in terms of the attrition loss (%)) of the catalyst, and the results of the ammoxidation reaction are shown in Table 2.

COMPARATIVE EXAMPLE 2

An ammoxidation catalyst was prepared in substantially the same manner as in Example 1, except that 1,666.7 g of an aqueous silica sol having an $SiO_2$ content of 30% by weight and an average primary silica particle diameter of 86 nm was used alone as a silica raw material and that the final calcination temperature was 550° C.

With respect to the obtained catalyst, a measurement of the pore distribution was performed. As a result, it was found that the cumulative pore volume of pores having a pore diameter of 80 Å or less was 0.000 cc/g, the cumulative pore volume of pores having a pore diameter of 1,000 Å or more was 0.271 cc/g, and the total pore volume of the catalyst was 0.354 cc/g. That is, the cumulative pore volume of pores having a pore diameter of 80 Å or less was 0.0%, and the cumulative pore volume of pores having a pore diameter of 1,000 Å or more was 76.6%, each based on the total pore volume of the catalyst.

Using 50 g of the obtained catalyst, an ammoxidation reaction of propylene was conducted. The contact time in the ammoxidation reaction was 3.9 (sec·g/cc). Results of the reaction were evaluated 24 hours after the start of the reaction. As a result, it was found that the conversion of propylene was 99.1%, and the yield of acrylonitrile was 84.5%.

50 g of the obtained catalyst was subjected to an attrition resistance test in accordance with the ACC method. As a result, the catalyst exhibited an attrition loss (%) as high as 7.18% as measured in the period of from 5 hour point to 20 hour point after the start of the attrition resistance test. Therefore, the attrition resistance test was discontinued 20 hours after the start of the attrition resistance test. The composition of the catalyst and the production conditions for the catalyst are shown in Table 1. The pore distribution and attrition resistance (in terms of the attrition loss (%)) of the catalyst, and the results of the ammoxidation reaction are shown in Table 2.

EXAMPLE 2

An ammoxidation catalyst comprised of a metal oxide supported on a silica carrier which was present in an amount of 50% by weight, based on the total weight of the metal oxide and the silica carrier, wherein the metal oxide had a metal composition represented by the formula:

$Mo_{12}Bi_{0.6}Ce_{0.75}Fe_{1.8}Ni_{5.0}Mg_{2.0}K_{0.09}Rb_{0.05}$ was prepared as follows.

833.3 g of an aqueous silica sol having an $SiO_2$ content of 30% by weight and an average primary silica particle diameter of 86 nm was mixed with 833.3 g of an aqueous silica sol having an $SiO_2$ content of 30% by weight and an average primary silica particle diameter of 12 nm, to thereby obtain a silica raw material. 56.0 g of bismuth nitrate [$Bi(NO_3)_3 \cdot 5H_2O$], 62.7 g of cerium nitrate [$Ce(NO_3)_3 \cdot 6H_2O$,] 140.0 g of iron nitrate [$Fe(NO_3)_3 \cdot 9H_2O$], 278.0 g of nickel nitrate [$Ni(NO_3)_2 \cdot 6H_2O$], 98.7 g of magnesium nitrate [$Mg(NO_3)_2 \cdot 6H_2O$], 1.75 g of potassium nitrate [$KNO_3$] and 1.42 g of rubidium nitrate [$RbNO_3$] were dissolved in 404.7 g of a 16.6% by weight aqueous nitric acid solution. The resultant solution was added to the above-obtained silica raw material to obtain a mixture. To the thus obtained mixture was added a solution of 407.9 g of ammonium paramolybdate [$(NH_4)_6Mo_7O_{24} \cdot 4H_2O$] in 821.6 g of water, to thereby obtain an aqueous raw material mixture. The thus obtained aqueous raw material mixture was fed to a parallel flow type spray-drying apparatus, in which the aqueous raw material mixture was atomized by means of a sprayer having a dish type rotor disposed above the central portion of a dryer of the spray-drying apparatus, and dried while maintaining the inlet temperature of the dryer at about 250° C. and the outlet temperature of the dryer at about 140° C., to thereby obtain particles (i.e., a dried catalyst precursor). The dried catalyst precursor was subjected to a preliminary calcination in air in an electric kiln at 350° C. for 1 hour and then subjected to a final calcination in air at 590° C. for 2 hours, thereby obtaining a catalyst.

With respect to the obtained catalyst, a measurement of the pore distribution was performed. As a result, it was found that the cumulative pore volume of pores having a pore diameter of 80 Å or less was 0.014 cc/g, the cumulative pore volume of pores having a pore diameter of 1,000 Å or more was 0.004 cc/g, and the total pore volume of the catalyst was 0.225 cc/g. That is, the cumulative pore volume of pores having a pore diameter of 80 Å or less was 6.2%, and the cumulative pore volume of pores having a pore diameter of 1,000 Å or more was 1.8%, each based on the total pore volume of the catalyst.

Using 50 g of the obtained catalyst, an ammoxidation reaction of propylene was conducted. The contact time in the ammoxidation reaction was 4.6 (sec·g/cc). Results of the reaction were evaluated 24 hours after the start of the reaction. As a result, it was found that the conversion of propylene was 99.2%, and the yield of acrylonitrile was 84.2%.

50 g of the obtained catalyst was subjected to an attrition resistance test in accordance with the ACC method. As a result, the catalyst exhibited an attrition loss (%) of 5.2%. The composition of the catalyst and the production conditions for the catalyst are shown in Table 1. The pore distribution and attrition resistance (in terms of the attrition loss (%)) of the catalyst, and the results of the ammoxidation reaction are shown in Table 2.

COMPARATIVE EXAMPLE 3

An ammoxidation catalyst was prepared in substantially the same manner as in Example 2, except that 1,250.0 g of an aqueous silica sol having an $SiO_2$ content of 30% by weight and an average primary silica particle diameter of 86 nm was mixed with 416.7 g of an aqueous silica sol having an $SiO_2$ content of 30% by weight and an average primary silica particle diameter of 12 nm, to thereby obtain a silica raw material (namely, the ratios of these two silica sols were changed as shown in Table 1), and that the final calcination temperature was 570° C.

With respect to the obtained catalyst, a measurement of the pore distribution was performed. As a result, it was found that the cumulative pore volume of pores having a pore diameter of 80 Å or less was 0.002 cc/g, the cumulative pore volume of pores having a pore diameter of 1,000 Å or more was 0.152 cc/g, and the total pore volume of the catalyst was 0.289 cc/g. That is, the cumulative pore volume of pores having a pore diameter of 80 Å or less was 0.7%, and the cumulative pore volume of pores having a pore diameter of 1,000 Å or more was 52.6%, each based on the total pore volume of the catalyst.

Using 50 g of the obtained catalyst, an ammoxidation reaction of propylene was conducted. The contact time in the ammoxidation reaction was 4.2 (sec·g/cc). Results of the reaction were evaluated 24 hours after the start of the reaction. As a result, it was found that the conversion of propylene was 99.2%, and the yield of acrylonitrile was 84.0%.

50 g of the obtained catalyst was subjected to an attrition resistance test in accordance with the ACC method. As a result, the catalyst exhibited an attrition loss (%) of 15.0%. The composition of the catalyst and the production conditions for the catalyst are shown in Table 1. The pore distribution and attrition resistance (in terms of the attrition loss (%)) of the catalyst, and the results of the ammoxidation reaction are shown in Table 2.

EXAMPLE 3

An ammoxidation catalyst comprised of a metal oxide supported on a silica carrier which was present in an amount of 50% by weight, based on the total weight of the metal oxide and the silica carrier, wherein the metal oxide had a metal composition represented by the formula:

$$Mo_{12}Bi_{0.3}Pr_{0.13}Nd_{0.47}Fe_2Ni_{5.4}Zn_{2.1}K_{0.08}Cs_{0.04}$$

was prepared as follows.

833.3 g of an aqueous silica sol having an $SiO_2$ content of 30% by weight and an average primary silica particle diameter of 58 nm was mixed with 1,250.0 g of an aqueous silica sol having an $SiO_2$ content of 20% by weight and an average primary silica particle diameter of 8 nm, to thereby obtain a silica raw material. 27.6 g of bismuth nitrate $[Bi(NO_3)_3.5H_2O]$, 5.68 g of praseodymium nitrate $[Pr(NO_3)_2]$, 39.1 g of neodymium nitrate $[Nd(NO_3)_3.6H_2O]$, 153.3 g of iron nitrate $[Fe(NO_3)_3.9H_2O]$, 297.9 g of nickel nitrate $[Ni(NO_3)_2.6H_2O]$, 118.5 g of zinc nitrate $[Zn(NO_3)_2.6H_2O]$, 1.54 g of potassium nitrate $[KNO_3]$ and 1.48 g of cesium nitrate $[CsNO_3]$ were dissolved in 403.1 g of a 16.6% by weight aqueous nitric acid solution. The resultant solution was added to the above-obtained silica raw material to obtain a mixture. To the thus obtained mixture was added a solution of 401.9 g of ammonium paramolybdate $[(NH_4)_6Mo_7O_{24}.4H_2O]$ in 809.6 g of water, to thereby obtain an aqueous raw material mixture. The thus obtained aqueous raw material mixture was fed to a parallel flow type spray-drying apparatus, in which the aqueous raw material mixture was atomized by means of a sprayer having a dish type rotor disposed above the central portion of a dryer of the spray-drying apparatus, and dried while maintaining the inlet temperature of the dryer at about 250° C. and the outlet temperature of the dryer at about 140° C., to thereby obtain particles (i.e., a dried catalyst precursor). The dried catalyst precursor was subjected to a preliminary calcination in air in an electric kiln at 350° C. for 1 hour and then subjected to a final calcination in air at 580° C. for 2 hours, thereby obtaining a catalyst.

With respect to the obtained catalyst, a measurement of the pore distribution was performed. As a result, it was found that the cumulative pore volume of pores having a pore diameter of 80 Å or less was 0.022 cc/g, the cumulative pore volume of pores having a pore diameter of 1,000 Å or more was 0.009 cc/g, and the total pore volume of the catalyst was 0.237 cc/g. That is, the cumulative pore volume of pores having a pore diameter of 80 Å or less was 9.3%, and the cumulative pore volume of pores having a pore diameter of 1,000 Å or more was 3.8%, each based on the total pore volume of the catalyst.

Using 50 g of the obtained catalyst, an ammoxidation reaction of propylene was conducted. The contact time in the ammoxidation reaction was 4.1 (sec·g/cc). Results of the reaction were evaluated 24 hours after the start of the reaction. As a result, it was found that the conversion of propylene was 99.1%, and the yield of acrylonitrile was 84.2%.

50 g of the obtained catalyst was subjected to an attrition resistance test in accordance with the ACC method. As a result, the catalyst exhibited an attrition loss (%) of 4.8%. The composition of the catalyst and the production conditions for the catalyst are shown in Table 1. The pore distribution and attrition resistance (in terms of the attrition loss (%)) of the catalyst, and the results of the ammoxidation reaction are shown in Table 2.

COMPARATIVE EXAMPLE 4

An ammoxidation catalyst was prepared in substantially the same manner as in Example 3, except that 2,500.0 g of an aqueous silica sol having an $SiO_2$ content of 20% by weight and an average primary silica particle diameter of 8 nm was used alone as a silica raw material and that the final calcination temperature was 610° C.

With respect to the obtained catalyst, a measurement of the pore distribution was performed. As a result, it was found that the cumulative pore volume of pores having a pore diameter of 80 Å or less was 0.0802 cc/g, the cumulative pore volume of pores having a pore diameter of 1,000 Å or more was 0.000 cc/g, and the total pore volume of the catalyst was 0.204 cc/g. That is, the cumulative pore volume of pores having a pore diameter of 80 Å or less was 39.3%, and the cumulative pore volume of pores having a pore diameter of 1,000 Å or more was 0.0%, each based on the total pore volume of the catalyst.

Using 50 g of the obtained catalyst, an ammoxidation reaction of propylene was conducted. The contact time in the ammoxidation reaction was 3.8 (sec·g/cc). Results of the reaction were evaluated 24 hours after the start of the reaction. As a result, it was found that the conversion of propylene was 99.1%, and the yield of acrylonitrile was 81.9%.

50 g of the obtained catalyst was subjected to an attrition resistance test in accordance with the ACC method. As a result, the catalyst exhibited an attrition loss (%) of 1.5%. The composition of the catalyst and the production conditions for the catalyst are shown in Table 1. The pore distribution and attrition resistance (in terms of the attrition loss (%)) of the catalyst, and the results of the ammoxidation reaction are shown in Table 2.

EXAMPLE 4

An ammoxidation catalyst comprised of a metal oxide supported on a silica carrier which was present in an amount of 35% by weight, based on the total weight of the metal oxide and the silica carrier, wherein the metal oxide had a metal composition represented by the formula:

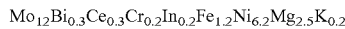

$Mo_{12}Bi_{0.3}Ce_{0.3}Cr_{0.2}In_{0.2}Fe_{1.2}Ni_{6.2}Mg_{2.5}K_{0.2}$ was prepared as follows.

37.0 g of bismuth nitrate $[Bi(NO_3)_3.5H_2O]$, 33.1 g of cerium nitrate $[Ce(NO_3)_3.6H_2O]$, 20.3 g of chromium nitrate $[Cr(NO_3)_3.9H_2O]$, 18.0 g of indium nitrate $[In(NO_3)_3.3H_2O]$, 123.2 g of iron nitrate $[Fe(NO_3)_3.9H_2O]$, 458.1 g of nickel nitrate $[Ni(NO_3)_2.6H_2O]$, 162.8 g of magnesium nitrate $[Mg(NO_3)_2.6H_2O]$ and 5.14 g of potassium nitrate $[KNO_3]$ were dissolved in 417.7 g of a 16.6% by weight aqueous nitric acid solution. The resultant solution was added to 1,166.7 g of an aqueous silica sol having an $SiO_2$ content of 30% by weight and an average primary silica particle diameter of 12 nm, to obtain a mixture. To the thus obtained mixture was added a solution of 538.3 g of ammonium paramolybdate $[(NH_4)_6Mo_7O_{24}.4H_2O]$ in 1,084.1 g of water, to thereby obtain an aqueous raw material mixture. The thus obtained aqueous raw material mixture was fed to a parallel flow type spray-drying apparatus, in which the aqueous raw material mixture was atomized by means of a sprayer having a dish type rotor disposed above the central portion of a dryer of the spray-drying apparatus, and dried while maintaining the inlet temperature of the dryer at about 250° C. and the outlet temperature of the dryer at about 140° C., to thereby obtain particles (i.e., a dried catalyst precursor). The dried catalyst precursor was subjected to a preliminary calcination in air in an electric kiln at 350° C. for 1 hour and then subjected to a final calcination in air at 560° C. for 2 hours, thereby obtaining a catalyst.

With respect to the obtained catalyst, a measurement of the pore distribution was performed. As a result, it was found that the cumulative pore volume of pores having a pore diameter of 80 Å or less was 0.020 cc/g, the cumulative pore volume of pores having a pore diameter of 1,000 Å or more was 0.013 cc/g, and the total pore volume of the catalyst was 0.210 cc/g. That is, the cumulative pore volume of pores having a pore diameter of 80 Å or less was 9.5%, and the cumulative pore volume of pores having a pore diameter of 1,000 Å or more was 6.2%, each based on the total pore volume of the catalyst.

Using 50 g of the obtained catalyst, an ammoxidation reaction of propylene was conducted. The contact time in the ammoxidation reaction was 4.2 (sec·g/cc). Results of the reaction were evaluated 24 hours after the start of the reaction. As a result, it was found that the conversion of propylene was 99.1%, and the yield of acrylonitrile was 84.5%.

50 g of the obtained catalyst was subjected to an attrition resistance test in accordance with the ACC method. As a result, the catalyst exhibited an attrition loss (%) of 3.5%. The composition of the catalyst and the production conditions for the catalyst are shown in Table 1. The pore distribution and attrition resistance (in terms of the attrition loss (%)) of the catalyst, and the results of the ammoxidation reaction are shown in Table 2.

COMPARATIVE EXAMPLE 5

An ammoxidation catalyst was prepared in substantially the same manner as in Example 4, except that 1,666.7 g of an aqueous silica sol having an $SiO_2$ content of 30% by weight and an average primary silica particle diameter of 12 nm was used alone as a silica raw material and that the final calcination temperature was 600° C.

With respect to the obtained catalyst, a measurement of the pore distribution was performed. As a result, it was found that the cumulative pore volume of pores having a pore diameter of 80 Å or less was 0.061 cc/g, the cumulative pore volume of pores having a pore diameter of 1,000 Å or more was 0.001 cc/g, and the total pore volume of the catalyst was 0.213 cc/g. That is, the cumulative pore volume of pores having a pore diameter of 80 Å or less was 28.6%, and the cumulative pore volume of pores having a pore diameter of 1,000 Å or more was 0.5%, each based on the total pore volume of the catalyst.

Using 50 g of the obtained catalyst, an ammoxidation reaction of propylene was conducted. The contact time in the ammoxidation reaction was 3.9 (sec·g/cc). Results of the reaction were evaluated 24 hours after the start of the reaction. As a result, it was found that the conversion of propylene was 99.0%, and the yield of acrylonitrile was 82.5%.

50 g of the obtained catalyst was subjected to an attrition resistance test in accordance with the ACC method. As a result, the catalyst exhibited an attrition loss (%) of 1.9%. The composition of the catalyst and the production conditions for the catalyst are shown in Table 1. The pore distribution and attrition resistance (in terms of the attrition loss (%)) of the catalyst, and the results of the ammoxidation reaction are shown in Table 2.

TABLE 1

| | Mo | Bi | Fe | C | D | E | G | Amount of silica carrier present in the catalyst (% by weight) | Average primary silica particle diameter of silica sol and the amount of silica sol (% by weight) | Final calcination temperature (° C.) |
|---|---|---|---|---|---|---|---|---|---|---|
| Ex. 1 | 12 | 0.45 | 1.8 | $Ni_2Co_3Mg_2$ | — | $Ce_{0.9}$ | $K_{0.09}Rb_{0.05}$ | 50 | 22 nm = 100 | 580 |
| Compara. Ex. 1 | 12 | 0.45 | 1.8 | $Ni_2Co_3Mg_2$ | — | $Ce_{0.9}$ | $K_{0.09}Rb_{0.05}$ | 50 | 12 nm = 100 | 590 |
| Compara. Ex. 2 | 12 | 0.45 | 1.8 | $Ni_2Co_3Mg_2$ | — | $Ce_{0.9}$ | $K_{0.09}Rb_{0.05}$ | 50 | 86 nm = 100 | 550 |
| Ex. 2 | 12 | 0.6 | 1.8 | $Ni_5Mg_2$ | — | $Ce_{0.75}$ | $K_{0.09}Rb_{0.05}$ | 50 | 86 nm:12 nm = 50:50 [1] | 590 |
| Compara. Ex. 3 | 12 | 0.6 | 1.8 | $Ni_5Mg_2$ | — | $Ce_{0.75}$ | $K_{0.09}Rb_{0.05}$ | 50 | 86 nm:12 nm = 75:25 [2] | 570 |
| Ex. 3 | 12 | 0.3 | 2 | $Ni_{5.4}Zn_{2.1}$ | — | $Pr_{0.13}Nd_{0.47}$ | $K_{0.08}Cs_{0.04}$ | 50 | 58 nm:8 nm = 50:50 [3] | 580 |
| Compara. Ex. 4 | 12 | 0.3 | 2 | $Ni_{5.4}Zn_{2.1}$ | — | $Pr_{0.13}Nd_{0.47}$ | $K_{0.08}Cs_{0.04}$ | 50 | 8 nm = 100 | 610 |
| Ex. 4 | 12 | 0.3 | 1.2 | $Ni_{6.2}Mg_{2.5}$ | $Cr_{0.2}In_{0.2}$ | $Ce_{0.3}$ | $K_{0.2}$ | 35 | 12 nm = 100 | 560 |
| Compara. Ex. 5 | 12 | 0.3 | 1.2 | $Ni_{6.2}Mg_{2.5}$ | $Cr_{0.2}In_{0.2}$ | $Ce_{0.3}$ | $K_{0.2}$ | 50 | 12 nm = 100 | 600 |

Note:
[1] $SiO_2$ having an average primary silica particle diameter of 86 nm: $SiO_2$ having an average primary silica particle diameter of 12 nm = 50% by weight: 50% by weight
[2] $SiO_2$ having an average primary silica particle diameter of 86 nm: $SiO_2$ having an average primary silica particle diameter of 12 nm = 75% by weight: 25% by weight
[3] $SiO_2$ having an average primary silica particle diameter of 58 nm: $SiO_2$ having an average primary silica particle diameter of 8 nm = 50% by weight: 50% by weight

TABLE 2

| | Pore volume (cc/g) | | | The ratios of the cumulative pore volume of pores having a pore diameter of 80 Å or less and the cumulative pore volume of pores having a pore diameter of 1,000 Å or more, based on the total pore volume of the catalyst | | Reaction results | | | Results of the attrition resistance test |
|---|---|---|---|---|---|---|---|---|---|
| | Pores having a pore diameter of 80 Å or less | Pores having a pore diameter of 1,000 Å or more | Total pore volume of the catalyst | Pores having a pore diameter of 80 Å or less | Pores having a pore diameter of 1,000 Å or more | Contact time (sec · g/cc) | Conversion | Yield of AN | Attrition loss |
| Ex. 1 | 0.005 | 0.012 | 0.232 | 2.2% | 5.2% | 4.3 | 99.0% | 84.0% | 5.7% |
| Compara. Ex. 1 | 0.058 | 0.001 | 0.22 | 26.4% | 0.5% | 3.7 | 99.1% | 82.4% | 2.9% |
| Compara. Ex. 2 | 0 | 0.271 | 0.354 | 0.0% | 76.6% | 3.9 | 99.1% | 84.5% | 7% (5-20 Hr) |
| Ex. 2 | 0.014 | 0.004 | 0.225 | 6.2% | 1.8% | 4.6 | 99.2% | 84.2% | 5.2% |
| Compara. Ex. 3 | 0.002 | 0.152 | 0.289 | 0.7% | 52.6% | 4.2 | 99.2% | 84.0% | 15.0% |
| Ex. 3 | 0.022 | 0.009 | 0.237 | 9.3% | 3.8% | 4.1 | 99.1% | 84.2% | 4.8% |
| Compara. Ex. 4 | 0.0802 | 0 | 0.204 | 39.3% | 0.0% | 3.8 | 99.1% | 81.9% | 1.5% |
| Ex. 4 | 0.02 | 0.013 | 0.21 | 9.5% | 6.2% | 4.2 | 99.1% | 84.5% | 3.5% |
| Comara. Ex. 5 | 0.061 | 0.001 | 0.213 | 28.6% | 0.5% | 3.9 | 99.0% | 82.5% | 1.9% |

INDUSTRIAL APPLICABILITY

The ammoxidation catalyst of the present invention exhibits not only high activity in producing the desired product but also high attrition resistance when used on a commercial scale. Therefore, the catalyst of the present invention is advantageous in that, when the catalyst of the present invention is used for performing a catalytic ammoxidation of propylene, isobutene or tert-butyl alcohol in a fluidized-bed reactor, acrylonitrile or methacrylonitrile can be produced stably in high yield.

The invention claimed is:

1. A particulate porous ammoxidation catalyst for use in producing acrylonitrile or methacrylonitrile by reacting propylene, isobutene or tert-butyl alcohol with molecular oxygen and ammonia in a fluidized-bed reactor, said catalyst comprising a metal oxide and a silica carrier having supported thereon said metal oxide, wherein said silica carrier is present in an amount of from 20 to 80% by weight, based on the total weight of said metal oxide and said silica carrier and wherein said metal oxide is represented by the following formula (1):

$$Mo_{12}Bi_aFe_bC_cD_dE_eF_fG_gO_n \qquad (1)$$

wherein:

C is at least one element selected from the group consisting of nickel, cobalt, manganese, zinc, magnesium, calcium, strontium and barium;

D is at least one element selected from the group consisting of chromium, tungsten, boron, aluminum, gallium, indium, phosphorus, antimony and tellurium;

E is at least one element selected from the group consisting of rare earth elements;

F is at least one element selected from the group consisting of ruthenium, rhodium, palladium, osmium, iridium and platinum;

G is at least one element selected from the group consisting of sodium, potassium, rubidium and cesium; and a, b, c, d, e, f, g and n are, respectively, the atomic ratios of bismuth (Bi), iron (Fe), C, D, E, F, G and oxygen (O), relative to 12 atoms of molybdenum (Mo), wherein:

a is from 0.05 to 7, b is from 0.1 to 7, c is from 0 to 12, d is from 0 to 5, e is from 0 to 5, f is from 0 to 0.2, g is from 0.01 to 5, and n is the number of oxygen atoms required to satisfy the valence requirements of the other component elements present, said catalyst having a particle diameter distribution wherein the amount of catalyst particles having a particle diameter of from 5 to 200 μm is from 90 to 100% by weight, based on the weight of said catalyst, and said catalyst having a pore distribution wherein the cumulative pore volume of pores having a pore diameter of 80 Å or less is not more than 20%, based on the total pore volume of said catalyst, and the cumulative pore volume of pores having a pore diameter of 1,000 Å or more is not more than 20%, based on the total pore volume of said catalyst.

2. The particulate porous ammoxidation catalyst according to claim 1, wherein said silica carrier is produced from a silica raw material comprising 40 to 100% by weight of (i) at least one silica sol having an average primary silica particle diameter of from 20 to 100 nm and 60 to 0% by weight of (ii) at least one silica sol having an average primary silica particle diameter of from 5 nm to less than 20 nm, wherein the total weight of said at least one silica sol (i) and said at least one silica sol (ii) is 100% by weight, each % by weight of a silica sol being expressed in terms of the weight of silica contained in the silica sol.

3. A method for producing the catalyst of claim 1, which comprises:

providing an aqueous raw material mixture containing compounds of the metal elements of the metal oxide represented by the formula (1), and containing a silica raw material, said silica raw material comprising 40 to 100% by weight of (i) at least one silica sol having an average primary silica particle diameter of from 20 to 100 nm and 60 to 0% by weight of (ii) at least one silica sol having an average primary silica particle diameter of from 5 nm to less than 20 nm, wherein the total weight of said at least one silica sol (i) and said at least one silica sol (ii) is 100% by weight, each % by weight of a silica sol being expressed in terms of the weight of silica contained in the silica sol, spray drying said aqueous raw material mixture to thereby obtain a dried catalyst precursor, and calcining said dried catalyst precursor, thereby obtaining the catalyst of claim 1.

4. The method according to claim 3, wherein said calcining comprises a preliminary calcination and a final calcination, wherein said preliminary calcination is performed at a temperature in the range of from 150 to 430° C. and said final calcination is performed at a temperature in the range of from 450 to 750° C.

5. A method for producing acrylonitrile or methacrylonitrile, comprising reacting propylene, isobutene or tert-butyl alcohol with molecular oxygen and ammonia in a fluidized-bed reactor using the catalyst of claim 1.

6. A method for producing acrylonitrile or methacrylonitrile, comprising reacting propylene, isobutene or tert-butyl alcohol with molecular oxygen and ammonia in a fluidized-bed reactor using the catalyst produced by the method of claim 3 or 4.

* * * * *

UNITED STATES PATENT AND TRADEMARK OFFICE
CERTIFICATE OF CORRECTION

PATENT NO.       : 7,473,666 B2
APPLICATION NO.  : 10/541393
DATED            : January 6, 2009
INVENTOR(S)      : Hiroyuki Yanagi et al.

It is certified that error appears in the above-identified patent and that said Letters Patent is hereby corrected as shown below:

Column 1, Line 7, change "PCTJP2004/102397" to --PCT/JP2004/002397--.

Signed and Sealed this

Twenty-fourth Day of March, 2009

JOHN DOLL
*Acting Director of the United States Patent and Trademark Office*